United States Patent [19]
Chen et al.

[11] Patent Number: 6,160,146
[45] Date of Patent: Dec. 12, 2000

[54] PROCESS FOR PREPARING TRIFLUOROARYLALUMINUM ETHERATES

[75] Inventors: Eugene Y. Chen; Jerzy Klosin, both of Midland; William J. Kruper, Jr., Sanford; Robert E. LaPointe, Midland, all of Mich.

[73] Assignee: The Dow Chemical Company, Midland, Mich.

[21] Appl. No.: 09/449,508

[22] Filed: Nov. 24, 1999

Related U.S. Application Data

[60] Provisional application No. 60/120,678, Feb. 19, 1999.

[51] Int. Cl.[7] .......................................... C07F 5/06
[52] U.S. Cl. ........................... 556/190; 556/187
[58] Field of Search ...................... 556/187, 190

[56] References Cited

U.S. PATENT DOCUMENTS 2,960,516  11/1960  Nobia et al. ............................. 556/170
5,602,269  2/1997  Biagini et al. ........................... 260/448

FOREIGN PATENT DOCUMENTS 1 057 600  3/1959  Germany .

OTHER PUBLICATIONS

Hair et al., Journal of American Chemical Society, vol. 121, No. 20, pp. 4922–4923, 1999.
Australian Lournal of Chemistry, vol. 16, pp. 794–8000 (1963).
Zeitschrift Fur Naturforschung, vol. 20b p. 5, (1965).
Journal of Chemical society, (1967), p. 2185.

*Primary Examiner*—Porfirio Nazario-Gonzalez

[57] ABSTRACT

The monoether adduct of a tri(fluoroaryl)aluminum compound is prepared by an exchange reaction between a trihydrocarbylaluminum compound and a tri(fluororaryl)borane compound in a hydrocarbon solvent in the presence of a $C_{1-6}$ aliphatic ether in an amount from 0.9 to 1.0 moles per mole of aluminum.

5 Claims, No Drawings

PROCESS FOR PREPARING TRIFLUOROARYLALUMINUM ETHERATES

CROSS-REFERENCE TO RELATED APPLICATION

This application claims benefit of priority from provisional application 60/120,678, filed Feb. 19, 1999.

BACKGROUND OF THE INVENTION

The present invention relates to a process for preparing trifluoroarylaluminum etherate compounds, especially tris(pentafluorophenyl)aluminum etherate compounds that are useful as catalyst activators for olefin polymerizations or in the synthesis of such activators. The process is particularly beneficially employed to prepare such compounds in improved isolated yields and reduced process complexity.

In U.S. Pat. No. 5,602,269, an improved method for preparing nonetherate containing complexes of fluoroaryl derivatives of aluminum, gallium or indium was disclosed. The process involved an exchange of the corresponding metal trialkyl with a fluoroaryl boron compound carried out in a hydrocarbon solvent in order to obtain the complex in its pure form without coordinated ether molecules. However, such non-coordinated aluminum complexes are known to be shock sensitive and difficult to handle.

Techniques for preparing triarylaluminum etherate compounds involve the use of Grignard reagents, as illustrated by U.S. Pat. No. 2,960,516, *Australian Journal of Chemistry*, vol.16, pages 794–800 (1963), DE-A 1,057,600, *Zeitschrift fur Naturforschung*, vol. 20b, page 5, (1965), and *Journal of the Chemical Society*, (1967), page 2185.

SUMMARY OF THE INVENTION

According to the present invention it has now been discovered that the exchange reaction between trihydrocarbyl aluminum and tri(fluororaryl)borane compounds in the presence of an aliphatic ether and a hydrocarbon diluent may be controlled to give either the monoether adduct of the tri(fluoroaryl)aluminum compound or the alumicinium borate salt etherate resulting from abstraction of one hydrocarbyl ligand group from the trihydrocarbylaluminum compound and ion pair formation between the resulting cation and anion. For high yields of the tri(fluoroaryl)aluminum compound, the total quantity of ether present in the reaction mixture should be from 0.9 to 1.0 moles per mole of aluminum, preferably from 0.95 to 1.0 moles per mole of aluminum. Conversely, for high yields of the borate salt, the total quantity of ether present in the reaction mixture should be at least 5.0 moles per mole of aluminum. When total quantities of ether between 1.0 and 5.0 moles per mole of aluminum are used, mixtures of both tri(fluoroaryl)aluminum etherate and the alumicinium borate salt etherate are formed. If quantities of ether less than the above amounts are employed, small quantities of the shock sensitive, ether free compound are likely to form. Most preferably, the amount of ether employed is 1.0 moles per mole of aluminum. Further preferably, the ether is a dialkylether containing from 1–6 carbons in each alkyl group.

DETAILED DESCRIPTION OF THE INVENTION

Preferably for generation of improved yields of the desired tri(fluoroaryl)aluminum etherate compound, the trihydrocarbylaluminum reagent is a trialkylaluminum compound containing from 4 to 10 carbons in each alkyl group, and most preferably is triisobutylaluminum or tri(t-butyl)aluminum. Moreover, although the reagents can be combined in any order, yields of the desired tri(fluoroaryl)aluminum etherate compound are highest when the tri(fluoroaryl)boron compound is added last to a previously formed mixture of the trihydrocarbyl aluminum compound and ether.

The foregoing process steps are summarized in the following scheme (A):

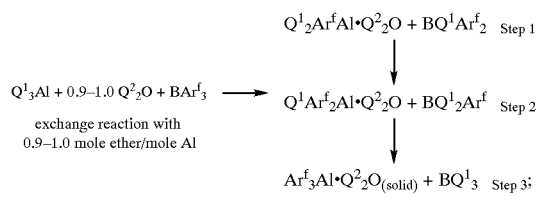

wherein, $Q^1$ is an aliphatic, aromatic or cycloaliphatic monofunctional radical containing from 1 to 20 carbon atoms, preferably a benzylic, or a linear or branched alkyl radical of from 1 to 20 carbons, more preferably $C_{4-20}$ alkyl, and most preferably isobutyl or tert-butyl;

$Ar^f$ is a fluorinated aryl group containing from 6 to 20 carbon atoms, preferably perfluoroaryl, most preferably perfluorophenyl; and $Q^2$ is $C_{1-6}$ alkyl.

The process steps in the presence of a 5:1 mole ratio or greater of ether are summarized in the following scheme (B):

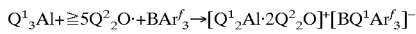

exchange reaction with >5.0 mole ether/mole Al
wherein $Q^1$, $Q^2$ and $Al^f$ are as previously defined.

The reaction according to scheme (A) or (B) is carried out in an aliphatic, cycloaliphatic or aromatic, hydrocarbon solvent, by combining the reagents either as solids or in liquid solutions in the above solvents in the presence of the desired amounts of the ether. Preferably, the reaction is carried out by dissolving the aluminum reagent in the solvent, preferably toluene or hexane, adding the desired quantity of ether, and finally adding, under stirring, to the solution thus obtained, the boron reagent, as a solid or in solution also in a hydrocarbon solvent. Due to the fact that the reagents and products are highly sensitive to oxygen or humidity, or both, all the reaction phases and subsequent isolation of the desired product, should be carried out under an inert gas.

The molar ratios of the reagents indicated in scheme (A) are maintained, for reasons of convenience, simplicity of the reaction and purity of the final product, at approximately 1:1. In fact, if an excess of the reagent $BAr^f_3$ is used, part of it must be recovered at the end of the reaction; making the isolation of the desired product in its pure state more difficult. If, on the contrary, an excess of the trihydrocarbylaluminum reagent or its etherate is used, the purity of the final product is jeopardized as well, since at the end of the reaction, besides the expected products, there will also be quantities of mixed products resulting from steps 1 and 2, as illustrated in Scheme (A).

The reaction temperature for the exchange is desirably within the range −20 to 100° C., preferably from 0 to 45° C., most preferably from 20 to 30° C. Suitable reaction times range from a few seconds to several hours, depending on the type of reagents and solvents used. The desired product can be recovered from the reaction mixture by filtration and subsequent drying under vacuum for several hours.

Tris(perfluoroaryl)aluminum compounds are strong Lewis acids which find utility in a variety of applications. Recently they have been found to be useful in the formation of compounds through ligand exchange with alumoxane that are olefin polymerization catalyst activators.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. Where stated, the term "room temperature" refers to a temperature from 20 to 25 C and the term "overnight" refers to a time from 12 to 18 hours.

EXAMPLES

Tris(perfluorophenyl)borane $(C_6F_5)_3B$ (FAB) was obtained as a solid from Boulder Scientific Inc. and used without further purification. Trimethylaluminum (TMA) in toluene or in hexanes, triethylaluminum (TEA) in hexanes, and triisobutylaluminum (TIBA) were purchased from Aldrich Chemical Co. Tris-(perfluorophenyl)aluminum (FAAL, as a toluene adduct) was prepared by exchange reaction between tris(perfluorophenyl) borane and trimethylaluminum, as reported by Biagini et.al., U.S. Pat. No. 5,602,269, and dinuclear $(C_6F_5)_3Al_2Me_3$ (FAAL·TMA) was prepared by exchange reaction between FAAL and TMA with a 1:1 ratio. All solvents were purified using the technique disclosed by Pangborn et al, *Organometallics*, 1996, 15, 1518–1520. All compounds, solutions, and reactions were handled under an inert atmosphere (dry box). All chemical shifts for $^{19}F$ NMR spectra were relative to a fixed external standard ($CFCl_3$) in benzene-$d_6$ or toluene-$d_8$, both of which were dried over Na/K alloy and filtered prior to use. $^1H$ and $^{13}C$ NMR shifts were referenced to internal solvent resonances and are reported relative to TMS.

For characterization purposes several aluminum compounds and etherate derivatives were prepared. Accordingly, in a glove box, FAAL (0.125 g, 0.20 mmol, toluene adduct) was dissolved in 20 mL (about 200 mmol) of dry diethyl ether in a flask and TMA (0.101 mL, 2.0 M in toluene, 0.20 mmol) was added dropwise. The reaction mixture was stirred for 2 h at room temperature, and the solvent was removed under reduced pressure to leave a sticky white solid in a quantitative yield. $^1H$ and $^{19}F$ NMR spectra of the product indicated the formation of a mixture of five species, including $(C_6F_5)_3Al \cdot Et_2O$, $(C_6F_5)_2AlMe \cdot Et_2O$, $(C_6F_5) AlMe_2 \cdot Et_2O$, $AlMe_3 \cdot Et_2O$, and $[AlMe_2 \cdot 2Et_2O]^+[(C_6F_5)_3AlMe]^-$. $(C_6F_5)_3Al \cdot Et_2O$: $^{19}F$ NMR ($C_7D_8$, 23° C.) at δ–122.60 (d, 6 F, o-F), –151.04 (t, 3 F, p-F), –160.69 (t, 6 F, m-F). $(C_6F_5)_2AlMe \cdot Et_2O$: $^1H$ NMR ($C_7D_8$, 23° C.) at δ–0.17 ppm; $^{19}F$ NMR ($C_7D_8$, 23° C.) δ–122.28 (d, 4 F, o-F), –153.25 (t, 2 F, p-F), –161.64 (t, 4 F, m-F). $(C_6F_5) AlMe_2 \cdot Et_2O$: $^1H$ NMR ($C_7D_8$, 23° C.) at δ–0.37 ppm; $^{19}F$ NMR ($C_7D_8$, 23° C.) at δ–122.79 (d, 2 F, o-F), –155.78 (t, 1 F, p-F), –162.43 (t, 2 F, m-F). $[AlMe_2 \cdot 2Et_2O]^+[(C_6F_5)_3AlMe]^-$: $^1H$ NMR ($C_7D_8$, 23° C.) at δ–0.52, –0.95 ppm; $^{19}F$ NMR ($C_7D_8$, 23° C.) at δ–121.59 (d, 6 F, o-F), –158.93 (t, 3 F, p-F), –164.15 (t, 6 F, m-F).

Reaction of $(C_6F_5)_3Al \cdot Et_2O$ with $AlMe_3 \cdot Et_2O$ in diethyl ether gave a similar result with a formation of the following four species, $(C_6F_5)_3Al \cdot Et_2O$, $(C_6F_5)_2AlMe \cdot Et_2O$, $(C_6F_5) AlMe_2 \cdot Et_2O$, and $[AlMe_2 \cdot 2Et_2O]^+[(C_6F_5)_3AlMe]^-$. The species $[AlMe_2 \cdot 2Et_2O]^+[(C_6F_5)_3AlMe]^-$ disappeared from the NMR spectra after a longer reaction time or after reaction at higher reaction temperature.

Likewise, reaction of $(C_6F_5)_3Al_2Me_3$ with diethyl ether generated a mixture of species $(C_6F_5)_2AlMe \cdot Et_2O$ and $(C_6F_5) AlMe_2 \cdot Et_2O$.

Example 1

Preparation of $(C_6F_5)_3Al \cdot Et_2O$ from $(C_6F_5)_3B$ and AlMe3

In a glove box, TMA (0.50 mL, 2.0 M in hexanes, 1.00 mmol) was dissolved in 20 mL of hexanes in a flask and diethyl ether (0.102 mL, 1.00 mmol) was added followed by addition of solid FAB (0.512 g, 1.00 mmol) in small portions. The reaction mixture turned cloudy during the FAB addition and became clear after stirring for a few minutes with a few oil drops sitting at the bottom of the flask. Precipitates started to form after stirring at room temperature for 1 h and the resulting suspension was stirred at this temperature for another 3 h. White solid which collected after the filtration was washed with hexanes twice and dried under vacuum to afford 0.28 g, 47 percent yield, of the desired product, $(C_6F_5)_3Al \cdot Et_2O$.

$^1H$ NMR ($C_6D_6$, 23° C.): δ 3.45 (m), 0.48 (m) ppm. $^{19}F$ NMR ($C_6D_6$, 23° C.): δ–122.68 (d, 6 F, o-F), –151.06 (t, 3 F, p-F), –160.75 (t, 6 F, m-F).

Example 2

Preparation of $(C_6F_5)_3Al \cdot Et_2O$ from $(C_6F_5)_3B$ and AlMe3

In a glove box, FAB (0.512 g, 1.00 mmol) was dissolved in 20 mL of dry hexanes in a flask and diethyl ether (0.102 mL, 1.00 mmol) was added, followed by addition of TMA (0.50 mL, 2.0 M in hexanes, 1.00 mmol). The reaction mixture turned cloudy during the TMA addition and became clear after stirring for a few minutes with a few oil drops sitting at the bottom of the flask. Precipitates started to form after stirring at room temperature for 1 h and the resulting suspension was stirred at this temperature for another 3 h. White solid which collected after the filtration was washed with hexanes twice and dried under vacuum to afford a similar yield of the desired product, FAAL·$Et_2O$.

The same reaction but with 1.5 equivalents of diethyl ether afforded a mixture of products as an oil, including the formation of $[AlMe_2 \cdot 2Et_2O]^+[(C_6F_5)_3BMe]^-$. When 5 equivalents of dibutyl ether were used for the same reaction, the only product, $[AlMe_2 \cdot 2Bu_2O]^+[(C_6F_5)_3BMe]^-$, was cleanly generated.

$^1H$ NMR ($C_6D_6$, 23° C.): δ 3.61 (m), 1.34 (m), 1.01 (m), and 0.77 (m) for coordinated $Bu_2O$, δ 0.90 and –0.75 ppm for Al—Me and B—Me, respectively. $^{19}F$ NMR ($C_6D_6$, 23° C.): δ–132.24 (d, 6 F, o-F), –164.99 (t, 3 F, p-F), –167.60 (t, 6 F, m-F).

Example 3

Preparation of $(C_6F_5)_3Al \cdot Et_2O$ from $(C_6F_5)_3B$ and $AlEt_3$

In a glove box, FAB (0.256 g, 0.50 mmol) was dissolved in 15 mL of dry hexanes in a flask and diethyl ether (0.051 mL, 0.50 mmol) was added, followed by addition of TEA (0.50 mL, 1.0 M in hexanes, 0.50 mmol). The reaction mixture turned cloudy during the TEA addition and became clear after stirring for a few minutes with a few oil drops sitting at the bottom of the flask. The resulting mixture was heated at reflux and stirred at this temperature for 6 h. The solution was then cooled to room temperature and the resulting suspension was stirred at this temperature overnight. White solid which collected after the filtration was washed with hexane twice and dried under vacuum to afford 0.22 g, 75 percent yield of the desired product, FAAL·Et$_2$O.

Example 4

Preparation of $(C_6F_5)_3$Al·Et$_2$O from $(C_6F_5)_3$B and Al(i-Bu)$_3$

In a glove box, TIBA (0.126 mL, 0.50 mmol) was dissolved in 20 mL of dry hexanes in a flask and diethyl ether (0.051 mL, 0.50 mmol) was added and followed by addition of solid FAB (0.256 g, 0.50 mmol) in small portions. The reaction mixture turned cloudy during the FAB addition and became clear after stirring for a few minutes with a few oil drops sitting at the bottom of the flask. Precipitates started to form after stirring at room temperature for 1.5 h and the resulting suspension was stirred at this temperature overnight. White solid which collected after the filtration was washed with hexanes twice and dried under vacuum to afford 0.255 g of the desired product FAAL·Et$_2$O. Yield: 85 percent.

Example 5

Preparation of $(C_6F_5)_3$Al·Et$_2$O from $(C_6F_5)_3$B and Al(i-Bu)$_3$

In a glove box, FAB (0.256 g, 0.50 mmol) was dissolved in 20 mL of dry hexanes in a flask and diethyl ether (0.051 mL, 0.50 mmol) was added, followed by addition of TIBA (0.126 mL, 0.50 mmol). The reaction mixture turned cloudy during the TIBA addition and became clear after stirring for a few minutes with a few oil drops sitting at the bottom of the flask. Precipitates started to form after stirring at room temperature for 1.5 h and the resulting suspension was stirred at this temperature overnight. White solid which collected after the filtration was washed with hexanes twice and dried under vacuum to afford 0.202 g (67 percent yield) of the desired product, FAAL·Et$_2$O. The same reaction in the presence of more than one equivalent of diethyl ether gave a milky solution from which no product could be isolated.

What is claimed is:

1. A process for preparing the monoether adduct of a tri(fluoroaryl)aluminum compound by means of an exchange reaction between a trihydrocarbyl aluminum compound or $C_{1-6}$ aliphatic etherate derivative thereof and a tri(fluororaryl)borane compound or $C_{1-6}$ aliphatic etherate derivative thereof, in the presence of a diluent comprising a hydrocarbon and optionally a $C_{1-6}$ aliphatic ether, said process comprising conducting the exchange reaction under condition such that the total quantity of $C_{1-6}$ aliphatic ether present in the reaction mixture is from 0.9 to 1.0 moles per mole of aluminum.

2. The process of claim 1 wherein the trihydrocarbyl aluminum reagent is a trialkylaluminum containing from 4 to 10 carbons in each alkyl group.

3. The process of claim 2 wherein the trialkylaluminum reagent is triisobutylaluminum or tri(t-butyl)aluminum.

4. The process of claim 1 wherein the tri(fluoroaryl)boron compound is added to a previously formed mixture of the trihydrocarbylaluminum compound and $C_{1-6}$ aliphatic ether.

5. The process of any one of claims 1–4 wherein the trihydrocarbylaluminum reagent is triisobutylaluminum and the tri(fluoroayrl)boron compound is tris (pentafluorophenyl)boron.

* * * * *